US006698330B1

(12) United States Patent
Witte et al.

(10) Patent No.: US 6,698,330 B1
(45) Date of Patent: Mar. 2, 2004

(54) INFRARED FRIEND OR FOE IDENTIFICATION SYSTEM

(75) Inventors: Arvel Benjamin Witte, Rolling Hills, CA (US); Arthur Karl Williams, Los Angeles, CA (US); Richard David Fleeter, Reston, VA (US)

(73) Assignee: Northrop Grumman Corporation, Los Angeles, CA (US)

( * ) Notice: Subject to any disclaimer, the term of this patent is extended or adjusted under 35 U.S.C. 154(b) by 1,826 days.

(21) Appl. No.: 07/068,501

(22) Filed: Jul. 1, 1987

(51) Int. Cl.[7] .............................. G01J 3/00; G01S 13/78

(52) U.S. Cl. ........................... 89/1.11; 250/340; 342/53

(58) Field of Search ................... 89/1.1, 1.11; 250/339, 250/340; 342/45, 53, 13

(56) References Cited

U.S. PATENT DOCUMENTS 3,169,726 A * 2/1965 Jackson .................... 342/53 X
3,641,344 A * 2/1972 Markle ........................ 250/339
3,780,615 A * 12/1973 Peyton et al. ................ 89/1.11
3,911,275 A * 10/1975 Dumbaugh ................. 250/339
3,922,673 A * 11/1975 Bishop ......................... 342/45
4,035,643 A * 7/1977 Barrett ................... 250/340 X
4,322,729 A * 3/1982 Honold et al. ................ 342/45
H333 H * 9/1987 Curtis ........................ 455/608

* cited by examiner

*Primary Examiner*—Michael J. Carone
*Assistant Examiner*—Gabriel S. Sukman

(57) ABSTRACT

The present invention resides in an infrared identification system for identifying military vehicles as friendly or hostile. The infrared identification system includes a seed introduction system, in each friendly vehicle, that introduces trace quantities of a particular seed formulation into the vehicle's exhaust. An infrared detection system, also in each friendly vehicle, detects the spectrally-discrete thermal emissions of the seed formulation to identify those vehicles having the thermal emissions as friendly. The infrared identification system provides rapid and positive friend or foe identification of land, sea and air vehicles at long ranges without being jammed, intercepted or mimicked.

22 Claims, 3 Drawing Sheets

INFRARED FRIEND OR FOE IDENTIFICATION SYSTEM

BACKGROUND OF THE INVENTION

This invention relates generally to systems for identifying military vehicles as friendly or hostile and, more particularly, to identification systems that rely on infrared emissions of the military vehicles.

Friend or foe identification systems used by military aircraft are generally radar-based systems, which operate in the microwave portion of the electromagnetic spectrum. Because the basic radar return from an aircraft is highly diffracted, the basic return cannot be used to positively identify the shape and, therefore, the type of aircraft. However, other portions of the radar return can be used to identify the type of aircraft. For example, a jet engine modulation (JEM) system analyzes the doppler shift of the radar return to determine the number and rotational velocities of the turbine blades in an aircraft's jet engine. From this, the type of jet engine can be identified and, once the jet engine has been identified, it is usually a simple matter to identify the type of aircraft. However, this system is not reliable as the enemy may be operating the same type of aircraft.

Another friend or foe identification system used by military aircraft utilizes a transponder to encode the radar return with the identity of the vehicle. However, this radar system can also be jammed and, in addition, can be intercepted or mimicked by the enemy. Accordingly, there has been a need for an improved identification system providing rapid and positive friend or foe identification of land, sea and air vehicles at long ranges without the possibility of being jammed, intercepted or mimicked. The present invention clearly fulfills this need.

SUMMARY OF THE INVENTION

The present invention resides in an infrared identification system for identifying military vehicles as friendly or hostile. Briefly, and in general terms, the present invention includes a seed introduction system, in each friendly vehicle, that introduces trace quantities of a particular seed formulation into the vehicle's exhaust. An infrared detection system, also in each friendly vehicle, detects the spectrally-discrete thermal emissions of the seed formulation to identify those vehicles having the thermal emissions as friendly.

More specifically, in a presently preferred embodiment of the invention, the seed introduction system introduces trace quantities of a particular seed formulation, which is changed preferably on a daily basis, into the vehicle's exhaust. The seed formulation can be introduced either continuously or upon interrogation by another friendly vehicle or other friendly source, such as a ground-based radar installation. When thermally excited, the seed formulation emits infrared radiation at known spectrally-discrete wavelengths. The infrared detection system can detect the faint infrared radiation all but buried in atmospheric and exhaust background noise, but only by knowing the particular seed formulation in use for that day. Detection of the infrared radiation confirms that the vehicle is friendly.

The seed introduction system includes a pressurized tank for storing the seed formulation of the day and a control system for injecting trace quantities of the seed formulation into the vehicle's exhaust. The control system includes a valve for releasing the seed formulation from the pressurized tank and a receiver for opening the valve when interrogated by a friendly source. Seed formulations that have been found to have suitable emissions within the infrared spectrum include the following halides:

hydrogen chloride (HCl)
hydrogen bromide (HBr)
hydrogen iodide (HI)
hydrogen fluoride (HF), the following hydrides:

sodium hydride (NaH)
calcium hydride (CaH)
potassium hydride (KH), and the following oxides:

beryllium oxide (BeO)
germanium oxide (GeO)
magnesium oxide (MgO)
selenium oxide (SeO)
aluminum oxide (AlO).

The infrared detection system includes a wide angle, optical lens and a standard, off-the-shelf infrared detector having a high sensitivity in the spectral region of interest. Because the infrared and visible spectrums are so close in frequency, an optical lens may be used to collect the observed radiation and concentrate it onto the sensitive infrared detector. The output of the infrared detector is filtered with a high-resolution bandpass filter that is centered at a frequency of one of the spectrally-discrete infrared emissions of the seed formulation of the day. The output of the bandpass filter is applied to a threshold trigger, which activates an indicator light when the total energy output by the bandpass filter exceeds a predetermined value, indicating that the interrogated vehicle is friendly.

It will be appreciated from the foregoing that the present invention provides a simple, jam proof system for identifying military vehicles as friendly or hostile that can easily be adapted to all types of air, land and sea vehicles. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENTS

Figure 1:
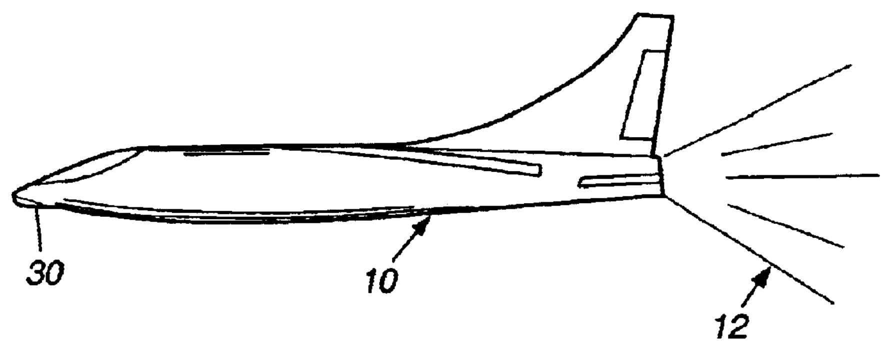
FIG. 1 is an elevational view of a jet fighter air aft and its exhaust plume.

As shown in the drawings for purposes of illustration, the present invention is embodied in an infrared identification system for identifying military vehicles as friendly or hostile. Friend or foe identification systems used by military aircraft are generally radar-based systems, which operate in the microwave portion of the electromagnetic spectrum.

Because the basic radar return from an aircraft is highly diffracted, the basic return cannot be used to positively identify the shape and, therefore, the type of aircraft. Other portions of the radar return can be used to identify the type of aircraft, but any radar return can easily be jammed, intercepted or mimicked by the enemy.

In accordance with the infrared identification system of the present invention, a seed introduction system, in each friendly vehicle, introduces trace quantities of a particular seed formulation into the vehicle's exhaust. An infrared detection system, also in each friendly vehicle, detects the spectrally-discrete thermal emissions of the seed formulation to identify those vehicles having the thermal emissions as friendly. The infrared identification system provides rapid and positive friend or foe identification of land, sea and air vehicles at long ranges without being jammed, intercepted or mimicked.

FIG. 1 illustrates a jet fighter aircraft 10 having an exhaust plume 12. Although a jet fighter aircraft is shown and described, any vehicle having an exhaust with a detectable percentage of infrared radiation can easily be adapted to utilize the present invention, including, for example, ships, tanks and other types of aircraft.

Figure 2:
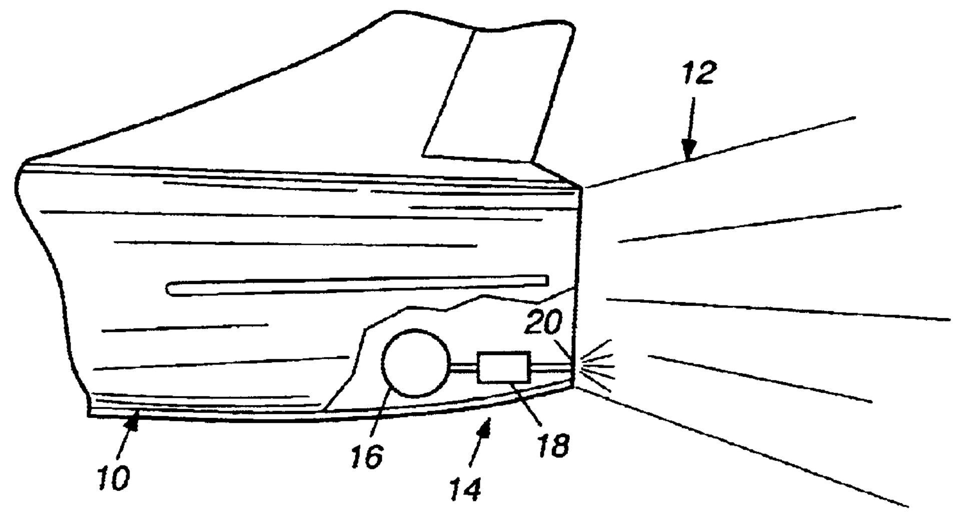
FIG. 2 is a fragmentary, exploded view of the jet fighter aircraft and its exhaust plume, showing a seed introduction system for introducing a seed formulation into the exhaust plume.
Figure 3:
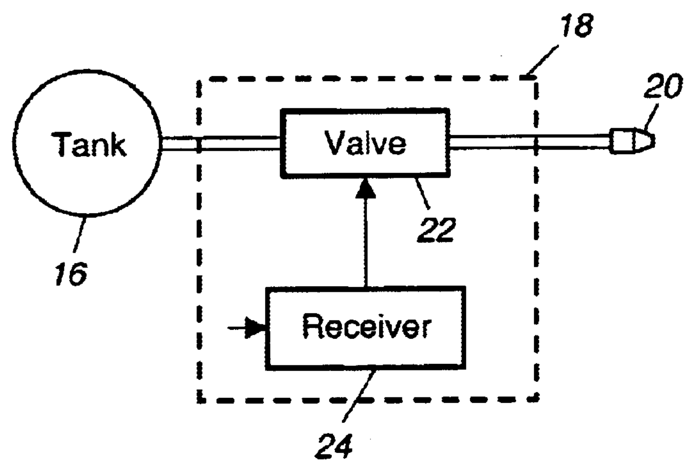
FIG. 3 is a schematic illustration of the seed introduction system.

FIG. 2 illustrates a seed introduction system 14 for introducing a particular seed formulation, which is changed preferably on a daily basis, into the exhaust plume 12 of the jet fighter aircraft 10. The seed formulation can be introduced either continuously or upon interrogation by another friendly vehicle or other friendly source, such as a ground-based radar installation. The seed introduction system 14 includes a pressurized tank 16 for storing the seed formulation in use for that day and a control system 18 for injecting trace quantities of the seed formulation, through a nozzle 20, into the exhaust plume 12. As shown more clearly in FIG. 3, the control system 18 includes a valve 22 for releasing the seed formulation from the pressurized tank 16 and a receiver 24 for opening the valve 22 when interrogated by a friendly source.

Figure 6:
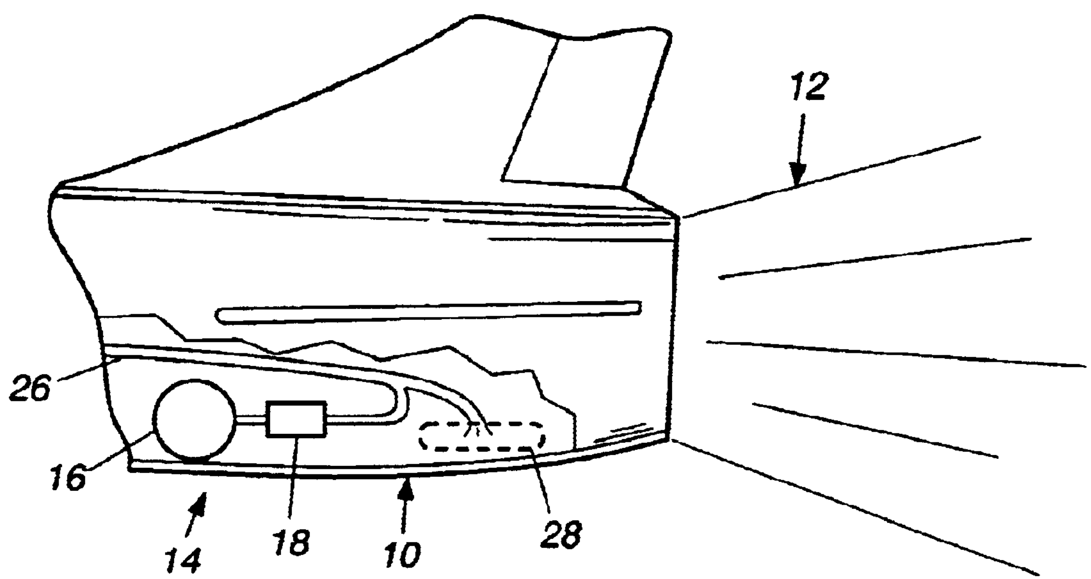
FIG. 6 is a fragmentary, exploded view of the jet fighter aircraft showing a seed introduction system for introducing a seed formulation into the fuel of the aircraft.
Figure 7:
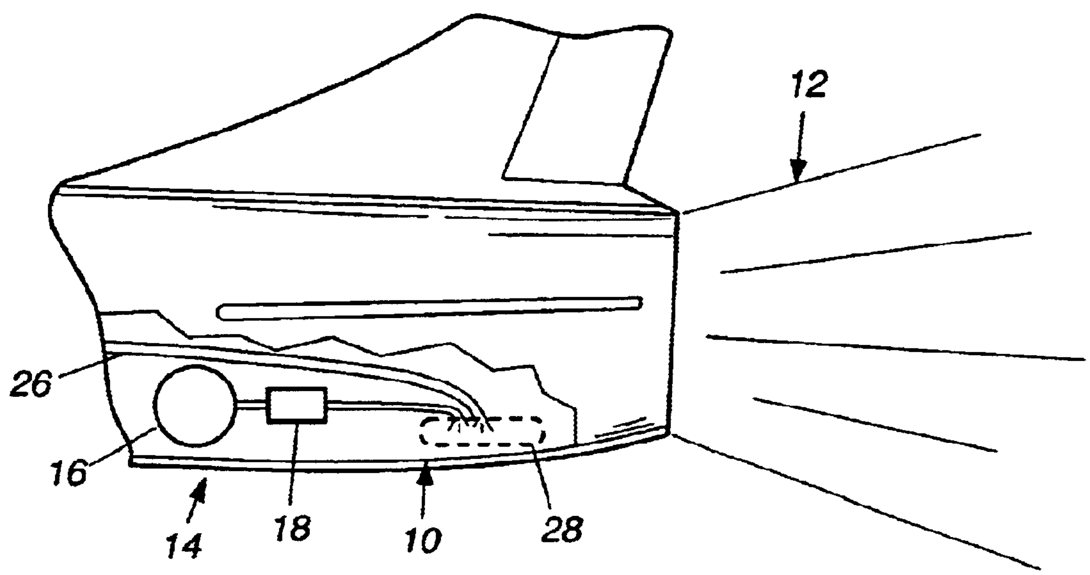
FIG. 7 is a fragmentary, exploded view of the jet fighter aircraft showing a seed introduction system for introducing a seed formulation into a combustor of the aircraft's jet engine.

Although the seed formulation is shown being injected directly into the exhaust plume 12 of the aircraft 10, the seed formulation can also be injected into the fuel 26 before being burned or injected into a combustor 28 of the aircraft's jet engine, as shown in FIGS. 6 and 7, respectively. Furthermore, instead of the seed formulation being changed by replacing the formulation in the pressurized tank 16, several tanks 16 can be located on board the aircraft 10 and the particular seed formulation of the day selected by a switch. Finally, if the seed formulation is injected into the exhaust plume 12 continuously, rather than upon interrogation by a friendly source, the interrogation signal is eliminated, resulting in a completely jam proof identification system.

When thermally excited, the seed formulation emits infrared radiation at known spectrally-discrete wavelengths. The infrared radiation is produced by transitions of electrons from states of higher energies to states of lower energies. The law of conservation of energy requires that, during each of these transitions, a photon or quantum of light is emitted from the electron with an energy corresponding to the difference between the initial and final energy states of the electron. The frequency of the emission is equal to this energy divided by Planck's constant. As the electrons reach higher energy levels, the spacing between energy levels becomes less and, therefore, the higher energy levels radiate with less energy and at lower frequencies. Accordingly, each particular seed formulation has a series of infrared emissions at different discrete wavelengths spanning the entire infrared spectrum.

To insure that the infrared radiation is all but buried in atmospheric and exhaust background noise and that the infrared radiation can only be detected by a friendly source with knowledge of the particular seed formulation in use for that day, only trace quantities of the seed formulation are introduced into the exhaust plume 12. These trace quantities preferably range in concentration from about 0.1 to 0.2% of the exhaust gas. This produces an optically thin exhaust plume, which allows all of the radiation from the gas to be detected.

The infrared portion of the electromagnetic spectrum extends from a wavelength of about 0.75 microns to a wavelength of 1000 microns, or from a frequency of about $4\times10^{14}$ Hz to a frequency of $3\times10^{11}$ Hz. Seed formulations that have been found to have suitable emissions within this spectrum include the following halides:

- hydrogen chloride (HCl)
- hydrogen bromide (HBr)
- hydrogen iodide (HI)
- hydrogen fluoride (HF).

These halides emit infrared radiation in the near-infrared region, between wavelengths of about 2 to 4 microns, or between frequencies of about $1.5\times10^{14}$ to $7.5\times10^{13}$ Hz. Other seed formulations that have been found to be suitable include the following hydrides:

- sodium hydride (NaH)
- calcium hydride (CaH)
- potassium hydride (KH)

and the following oxides:

- beryllium oxide (BeO)
- germanium oxide (GeO)
- magnesium oxide (MgO)
- selenium oxide (SeO)
- aluminum oxide (AlO).

These seed materials emit infrared radiation in the intermediate-infrared region, between wavelengths of about 8 to 11 microns, or between frequencies of about $3.75\times10^{13}$ to $2.75\times10^{13}$ Hz. All of the above seed formulations also emit infrared radiation in the far-infrared region, between wavelengths of about 20 to 1000 microns, or between frequencies of about $1.5\times10^{13}$ to $3\times10^{11}$ Hz.

Figure 4:
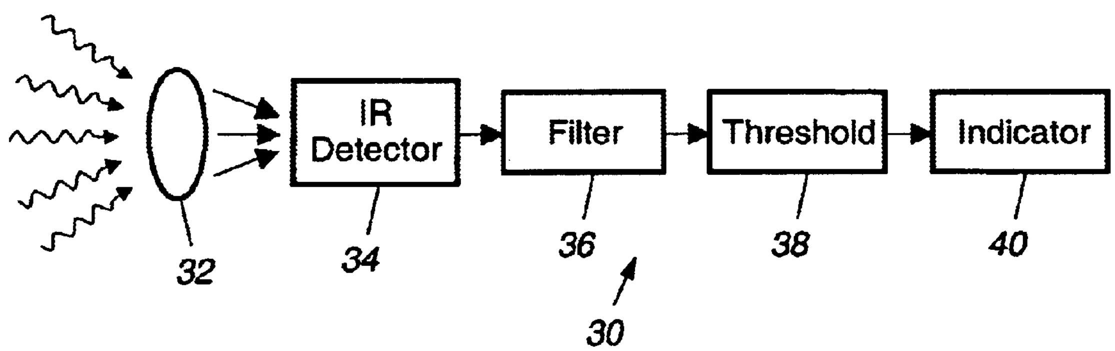
FIG. 4 is a schematic illustration of an infrared detector for detecting the spectrally-discrete thermal emissions of the seed formulation introduced into the exhaust plume.

FIG. 4 illustrates an infrared detection system 30 for identifying the aircraft 10 as friendly or hostile. The detection system 30 includes a wide angle, optical lens 32 and a standard, off-the-shelf infrared detector 34 having a high sensitivity in the spectral region of interest. Because the infrared and visible spectrums are so close in frequency, an optical lens may be used to collect the observed radiation and concentrate it onto the sensitive infrared detector 34. The output of the infrared detector 34 is filtered with a high-resolution bandpass filter 36 that is centered at a frequency of one of the spectrally-discrete infrared emissions of the seed formulation of the day. The output of the bandpass filter 36 is applied to a threshold trigger 38, which activates an indicator light 40 when the total energy output by the bandpass filter 36 exceeds a predetermined value, indicating that the interrogated aircraft is friendly.

The bandpass filter 36 is preferably a bank of high-resolution filters centered at the frequencies of the spectrally-discrete infrared emissions of the available seed formulations, with a switch for selecting the appropriate filter for the seed formulation of the day. Alternatively, the bandpass filter 36 is a single filter that can be tuned to the frequency of one of the spectrally-discrete infrared emissions of the seed formulation.

Figure 5:
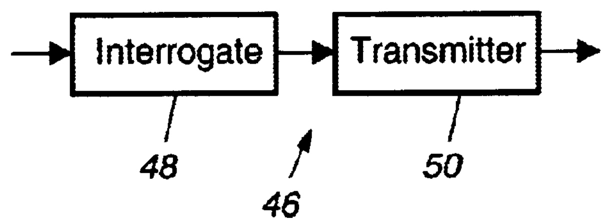
FIG. 5 is a schematic illustration of an interrogation circuit.

FIG. 5 shows an interrogation system 46, located with the infrared detection system 30, which causes trace quantities of the seed formulation to be introduced into the exhaust plume 12 of the jet fighter aircraft 10. The interrogation system 46 includes an interrogate switch 48 and a transmitter 50 that is activated by the interrogate switch 48. The transmitter 50 emits a coded radio signal, which is received by the receiver 24 in aircraft 10, causing valve 22 to open, thus releasing the seed formulation.

From the foregoing, it will be appreciated that the present invention provides a simple, jam proof system for identifying military vehicles as friendly or hostile that can easily be adapted to all types of air, land and sea vehicles. Although several preferred embodiments of the invention have been shown and described, it will be apparent that other adaptations and modifications can be made without departing from the spirit and scope of the invention. Accordingly, the invention is not to be limited, except as by the following claims.

We claim:

1. An infrared identification system for identifying military vehicles as friendly or hostile, comprising:

means for introducing trace quantities of a seed formulation into the exhaust of a friendly vehicle; and means for detecting the spectrally-discrete thermal emissions of the seed formulation to identify the vehicle as friendly.

2. The identification system as set forth in claim 1, wherein the detecting means includes:

an infrared detector;

an optical lens for collecting and concentrating infrared radiation from the vehicle onto the infrared detector;

a high-resolution bandpass filter centered at a frequency of one of the spectrally-discrete thermal emissions of the seed formulation;

a threshold trigger; and indicating means;

wherein the threshold trigger activates the indicating means when the total energy output by the bandpass filter exceeds a predetermined value, thereby indicating that the vehicle is friendly.

3. The identification system as set forth in claim 1, wherein the seed formulation is selected from a group consisting of the halides hydrogen chloride (HCl), hydrogen bromide (HBr), hydrogen iodide (HI) and hydrogen fluoride (HF).

4. At The identification system as set forth in claim 1, wherein the seed formulation is selected from a group consisting of the hydrides sodium hydride (NaH), calcium hydride (CaH) and potassium hydride (KH).

5. The identification system as set forth in claim 1, wherein the seed formulation is selected from a group consisting of the oxides beryllium oxide (BeO), germanium oxide (GeO), magnesium oxide (MgO), selenium oxide (SeO) and aluminum oxide (AlO).

6. The identification system as set forth in claim 1, wherein the trace quantities of the seed formulation range in concentration from approximately 0.1 to 2% of the exhaust of the vehicle.

7. The identification system as set forth in claim 1, wherein the introducing means includes:

a pressurized tank for storing the seed formulation;

a valve for releasing the seed formulation from the tank; and a nozzle for injecting the seed formulation into a combustor of an engine of the vehicle.

8. The identification system as set forth in claim 1, wherein the introducing means includes:

a pressurized tank for storing the seed formulation;

valve for releasing the seed formulation from the tank; and a nozzle for injecting the seed formulation into the fuel before being burned in an engine of the vehicle.

9. The identification system as set forth in claim 1, wherein the -introducing means includes:

a pressurized tank for storing the seed formulation;

a valve for releasing the seed formulation from the tank; and a nozzle for injecting the seed formulation into the exhaust of the vehicle.

10. The identification system as set forth in claim 9, and further including a receiver for opening the valve when interrogated by a friendly source.

11. A method for identifying military vehicles as friendly or hostile, comprising the steps of:

introducing trace quantities of a seed formulation into the exhaust of a friendly vehicle; and detecting the spectrally-discrete thermal emissions of the seed formulation to identify the vehicle as friendly.

12. The identifying method as set forth in claim 11, wherein the step of detecting includes the steps of:

concentrating infrared radiation from the vehicle onto an infrared detector with an optical lens;

filtering the output of the infrared detector with a high-resolution bandpass filter centered at a frequency of one of the spectrally-discrete thermal emissions; and indicating that the vehicle is friendly when the total energy output by the bandpass filter exceeds a predetermined value.

13. The identifying method as set forth in claim 11, wherein the seed formulation is selected from a group consisting of the halides hydrogen chloride (HCl), hydrogen bromide (HBr), hydrogen iodide (HI) and hydrogen fluoride (HF).

14. The identifying method as set forth in claim 11, wherein the seed formulation is selected from a group consisting of the hydrides sodium hydride (NaH), calcium hydride (CaH) and potassium hydride (KH).

15. The identifying method as set forth in claim 11, wherein the seed formulation is selected from a group consisting of the oxides beryllium oxide (BeO), germanium oxide (GeO), magnesium oxide (MgO), selenium oxide (SeO) and aluminum oxide (AlO).

16. The identifying method as set forth in claim 11, wherein the trace quantities of the seed formulation range in concentration from approximately 0.1 to 2% of the exhaust of the vehicle.

17. The identifying method as set forth in claim 11, wherein the step of introducing includes the steps of:

storing the seed formulation in a pressurized tank;

releasing the formulation from the tank with a valve; and injecting the seed formulation into the exhaust of the vehicle with a nozzle.

18. The identifying method as set forth in claim 17, wherein the seed formulation is injected into a combustor of an engine of the vehicle.

19. The identifying method as set forth in claim 17, wherein the seed formulation is injected into the fuel before being burned in an engine of the vehicle.

20. The identifying method as set forth in claim 17, wherein the seed formulation is injected into the exhaust of the vehicle as the exhaust exits the vehicle.

21. The identifying method as set forth in claim 17, wherein the seed formulation is injected into the exhaust of the vehicle only when interrogated by a friendly source.

22. The identifying method as set forth in claim 17, wherein the seed formulation is injected into the exhaust of the vehicle continuously.

* * * * *